United States Patent [19]
Onoda et al.

[11] 3,959,352
[45] May 25, 1976

[54] PROCESS FOR PREPARING A CARBOXYLIC ESTER

[75] Inventors: Takeru Onoda; Keisuke Wada, both of Yokohama; Masayuki Otake, Tokyo, all of Japan

[73] Assignee: Mitsubishi Chemical Industries Ltd., Tokyo, Japan

[22] Filed: Mar. 7, 1975

[21] Appl. No.: 556,265

[30]    Foreign Application Priority Data
    Mar. 12, 1974    Japan.................................. 49-28416
    July 10, 1974    Japan.................................. 49-79007

[52] U.S. Cl. ............................ 260/479 R; 252/430; 260/488 CD; 260/497 A
[51] Int. Cl.² ......................................... C07C 67/05
[58] Field of Search ................................ 260/479 R

[56]            References Cited
              UNITED STATES PATENTS
3,644,486    2/1972    Boldt et al. ........................... 260/479
3,646,111    2/1972    Hornig et al. ......................... 260/479
3,651,101    3/1972    Boldt et al. ........................... 260/479
3,725,462    4/1973    Boldt et al. ........................... 260/479

Primary Examiner—James A. Patten
Attorney, Agent, or Firm—Oblon, Fisher, Spivak, McClelland & Maier

[57]            ABSTRACT

A carboxylic ester is prepared by reacting a hydrocarbon selected from monoolefins having 2 to 6 carbon atoms, benzene, toluene and xylene with an aliphatic saturated carboxylic acid having 2 to 4 carbon atoms and molecular oxygen in the vapor phase in the presence of a supported solid catalyst of palladium metal, an antimony component and a carboxylic acid salt of alkali metal, alkaline earth metal, zinc, cadmium, lead or tin, with the improvement comprising: adding said antimony compound to the support of said catalyst by dipping a carrier into an aqueous solution of a water-soluble antimony compound selected from the group consisting of antimonic acid, antimonates and antimony complexes of organic acids.

21 Claims, No Drawings

PROCESS FOR PREPARING A CARBOXYLIC ESTER

BACKGROUND OF THE INVENTION

1. Field of the Invention

The present invention relates to a process for preparing a carboxylic ester by carboxylating an olefin such as ethylene, propylene, butene, or the like in an aromatic hydrocarbon such as benzene, toluene, xylene, or the like in the presence of molecular oxygen and an aliphatic carboxylic acid, utilizing an improved catalyst.

2. Description of the Prior Art

It is known that noble metals of Group VIII of the Periodic Table, especially palladium, are effective as catalysts for the above-mentioned reaction (for example, Japanese Patent Publication No. 13081/1967). It also is known that bismuth and gold compounds, tin salts, organic phosphorous compounds and iron salts can be used as promoters for improving the catalytic activity of these catalysts (for example, U.S. Pat. No. 3,547,982 and Japanese Patent Preliminary Disclosure No. 18843/1972). Moreover, it has been customary to add a carboxylic acid salt of a metal of Group 1A or 2A of the Periodic Table to the catalyst as an additional activator. However, the above-mentioned catalyst combinations have not been sufficiently effective to permit industrial use of the reaction. Also, it has been attempted to increase the catalytic activity and lifetime of palladium since the latter is so expensive. In vapor phase reactions, the result of such attempts usually is a decrease in the catalytic activity after only a short period of operation.

It would be most desirable, therefore, to have a catalyst which has both high activity and a long lifetime.

CROSS-REFERENCE TO RELATED APPLICATIONS

The present inventors have filed a U.S. application, Ser. No. 475,894, filed June 3, 1974, in which a process is claimed for preparing a phenyl ester and/or phenol by reacting benzene, a carboxylic acid, and molecular oxygen in the presence of a catalyst which is similar to the catalyst used in the present invention.

Applicants have also filed another application, Ser. No. 548,779, on Feb. 10, 1975. This application is concerned with the preparation of an aromatic compound with a hydroxymethyl group on the aromatic ring by reaction of an aromatic compound with a methyl group on its ring, an aliphatic carboxylic acid and gaseous $O_2$ in the presence of a catalyst which also is similar to the catalyst used in the present invention.

SUMMARY OF THE INVENTION

Accordingly, one object of the present invention is to provide a process for preparing a carboxylic ester, avoiding the above-mentioned disadvantages, by using a catalyst having high catalytic activity and long catalytic lifetime to react an olefin, e.g., ethylene, propylene, butene or an aromatic hydrocarbon, e.g., benzene, toluene, xylene with molecular oxygen and an aliphatic carboxylic acid.

Another object of the invention is to provide a catalyst having high catalytic activity and long catalytic life.

Briefly, these and other objects of this invention, as will hereinafter become more readily apparent, have been attained by the finding that antimony is an excellent promoter for such catalysts. The antimony component is supported on a carrier by dipping the carrier into an aqueous solution of a water soluble antimony compound selected from antimonic acid, antimonates and antimony complexes of organic acid. The complete solid catalyst which consists of the carrier supporting palladium metal, antimony, usually in the form of an oxide, and a carboxylic acid salt of alkali metal, alkaline earth metal, zinc, cadmium, lead or tin, is used in the preparation of a carboxylic ester by reacting an olefin or an aromatic hydrocarbon with molecular oxygen and an aliphatic carboxylic acid. It is especially preferable to use the catalyst prepared by using a carrier supporting said antimony component and then calcinating it at 500°–900°C in an oxygen-containing gas. The antimony component should be present in 0.05–8 gram-atom to 1 gram-atom of palladium.

DETAILED DESCRIPTION OF THE PREFERRED EMBODIMENTS

The catalyst used for the process of the invention contains palladium metal, an antimony component and a carboxylic salt of an alkali metal, an alkaline earth metal, zinc, cadmium, lead or tin. Various carriers used for industrial purposes can be used. Suitable carriers include silica, alumina, silica-alumina active carbon, diatomaceous earth, titania, zeolite or the like. It is especially preferred to use silica. The palladium can be supported on the carrier by dipping it into an aqueous solution of a palladium compound and drying and reducing the compound by a suitable method. Suitable palladium compounds include the various palladium compounds customarily used for preparation of palladium catalysts such as palladium chloride, palladium acetate, palladium nitrate, or sodium palladium chloride. When a solution of palladium chloride in conc-HCl is used for the preparation of the catalyst, it is preferred to support the antimony component after supporting the palladium component on the carrier. If the carrier is dipped in the solution of palladium chloride in conc-HCl after supporting the antimony component on the carrier, the antimony component may be converted to antimony chloride.

The invention is characterized by the use of a water soluble antimony compound for the preparation of the catalyst. Suitable water soluble antimony compounds include oxygen-containing components such as antimonic acid, meta-antimonic acid, pyro-antimonic acid, condensed antimonic acid and salts thereof; antimony complexes of an organic acid such as tartaric acid, oxalic acid, glycolic acid or a salt thereof, e.g., antimonyl potassium tartarate. No halogen should be present as a main component in the antimony compounds. The antimony compounds can be used in the form of an aqueous solution. It is possible to prepare a uniform solution when a sparingly soluble antimony compound is used by adding it to an aqueous solution of an organic acid such as tartaric acid, oxalic acid, glycolic acid or a salt thereof. When the carrier is dipped into the uniform aqueous solution, the antimony compound is easily and uniformly supported on the carrier. Moreover, in comparison with the catalysts prepared by using antimony trichloride, the present catalyst has excellent characteristics of high catalytic activity, high mechanical strength and high abrasive resistance.

The third component of the catalyst is selected from the carboxylic acid salts of alkali metals, alkaline earth metals, zinc, cadmium, lead and tin. Suitable carboxylic acid salts include aliphatic carboxylates such as formate, acetate, propionate, etc. It is preferred to use a salt of the carboxylic acid which is being used as the raw material for the carboxylation. When an alkali metal salt or an alkaline earth metal salt of antimonic acid or a complex of an organic acid is used as the water soluble antimony compound, it is possible to prepare the catalyst without the third component. The alkali metal or alkaline earth metal in the antimony compounds is supported on the carrier together with the antimony component from the aqueous solution, and the metal may be converted to the corresponding metal oxide in the calcination. In the subsequent carboxylation, the metal oxide may be converted to the corresponding aliphatic carboxylic acid salt by contacting with the feed gas containing the aliphatic carboxylic acid. It is also possible to support carboxylic acid salts of alkali metal, alkaline earth metal, zinc, cadmium, lead or tin as a third component by conventional methods after removing the alkali metal ion or alkaline earth metal ion derived from the antimony compound. For example, the antimony compound is supported on a carrier and the product is heated to convert the water soluble antimony compound to a water insoluble antimony compound such as antimony oxide. The product is washed with water, acid or ammonia water to selectively remove the alkali metal ion or alkaline earth metal ion. The method is preferably attained by using an aqueous solution of hydrazine with ammonia in the step wherein palladium is supported by reduction after the support of the antimony component.

The carrier supporting the antimony component is preferably calcined to convert the antimony component to antimony oxide. By calcining at high temperature, it is possible to improve the catalytic characteristics by firmly bonding the antimony component to the carrier while decomposing and removing the organic acid component in the antimony compound. The calcination is preferably conducted in the presence of an oxygen-containing gas such as air at a temperature of preferably 500°–900°C, especially 600°–800°C. When the calcination temperature is lower, the decomposition of the antimony compound, that is, the removal of the organic acid component, is incomplete. On the other hand, when the calcination temperature is higher, the mechanical strength of the catalyst is deteriorated. Also, occasionally the surface area of the carrier is decreased, whereby high catalytic activity is difficult to attain. The calcination may be performed for longer than 30 minutes after reaching the predetermined temperature.

Regarding the supporting of the palladium, the antimony component and the carboxylic acid salt of alkali metals, alkaline earth metals, zinc, cadmium, lead or tin, it is possible to support all three components at the same time or in the desirable sequential order. It is possible to calcine it immediately after supporting the antimony compound when the sequential supporting method is used. For example, it is possible to first support the antimony compound on the carrier and calcine it at the appropriate temperature in the presence of molecular oxygen. Subsequently, the palladium component and the third component can be supported. The order for supporting the three components can be changed. The optimum order is to support the palladium component and the antimony component and then to calcine the product followed by reduction of the palladium component and supporting of the third component, e.g., zinc acetate.

The concentrations of the components can be selected from broad ranges. The content of palladium metal on the carrier is preferably 0.1–20% by weight. The antimony component is combined to the extent of 0.05–8 gram-atom, preferably 0.5–8 gram-atom, of Sb to one gram-atom of palladium metal. The amount of the carboxylic acid salt of alkali metal, alkaline earth metal, zinc, cadmium, lead or tin, is usually 0.1–8 mole, preferably 0.5–4 mole to 1 gram-atom of palladium metal.

The effective forms of the palladium component and the antimony component in the catalyst are not clearly known. However, it is expected that the palladium component is mostly in the form of palladium metal and the antimony component is primarily in the form of antimony oxide with a small part consisting of an antimony-palladium alloy.

It is possible to use a palladium compound per se for the reaction. In this case, the palladium compound is easily reduced to palladium metal in the reaction for preparing the carboxylic ester by the olefin such as ethylene, propylene, butene, etc. Thus, it is preferred to previously reduce the palladium compound to palladium metal in the preparation of the catalyst. Conventional reduction methods can be employed, for example, the wet method using formalin or hydrazine, or the dry method using a reducing gas, e.g., hydrogen, methanol, etc. However, when the antimony component is coexistant, severe reduction conditions should be avoided since excessive reduction can adversely affect at least the preliminary catalytic activity. This is probably caused by prevention of effective oxidizing conditions for the antimony. For example, in the reduction by using hydrogen, it is especially preferable to reduce at lower than 200°C.

The starting materials for preparing the carboxylic esters include hydrocarbons selected from olefins having 2–6 carbon atoms, aromatic compounds such as benzene, methyl substituted aromatic compounds and aliphatic carboxylic acids and molecular oxygen. Suitable methyl substituted aromatic compounds include methyl substituted benzene such as toluene, o-, m-, p-xylene, and methyl substituted polycyclic aromatic hydrocarbons such as methyl naphthalene. It is especially preferable to use toluene and xylene. The methyl substituted aromatic compounds can have an inert group such as an hydroxyl group, an alkoxy group, a carboxyl group, or an alkyl group having 2 or more carbon atoms. Various aliphatic carboxylic acids can also be used. In the industrial process, a lower saturated aliphatic carboxylic acid havin 2–4 carbon atoms such as acetic acid, propionic acid, butyric acid or the like is advantageous. It is especially preferred to use acetic acid.

The reaction is normally conducted in the vapor phase. Of course, the reaction may be performed in the liquid phase. However, it is not preferred to conduct the reaction in the liquid phase because the catalytic component of the carboxylic acid salt of alkali metal, alkaline earth metal, zinc, cadmium, lead or tin becomes dissolved in the liquid phase since the carboxylic acid is present in the reaction system. The reaction can be performed in any desirable system, such as a fixed bed system, a fluidized bed system, or the like. A fixed bed multi-pipe reactor is especially preferable to perform the highly exothermic reaction safely.

The molecular oxygen used in the reaction can be pure oxygen as well as oxygen diluted with an inert gas such as air. The amount of oxygen may vary, and is usually outside of the explosive range. It is preferably present in 1–50 mole percent of the total gaseous components. The reaction can be performed under atmospheric pressure or up to a pressure of several tens of atmospheres. It may be performed under even higher pressure or lower pressure, if desirable.

The preferred reaction temperature is dependent upon the boiling points of the starting materials, the reaction pressure and the concentration ratio of the starting materials since the reaction system must be maintained in vapor phase. It is usually higher than 130°C. Taking into account the reaction velocity and side reactions, the preferred reaction temperature ranges from 140°–250°C.

The molar ratio of the hydrocarbon such as the monoolefins having 2–6 carbon atoms, benzene, toluene, xylene, etc. to the aliphatic carboxylic acid can be selected from a broad range. Preferable molar ratios of the hydrocarbon to the carboxylic acid are 1 :0.5–10, preferably 1 :1–10. An excess of the carboxylic acid is preferred for extending the catalytic life. The amount of oxygen selected is outside the explosive range of oxygen, and can be less than or in excess of the stoichiometric amount relative to the hydrocarbon.

Having generally described the invention, a more complete understanding can be obtained by reference to certain specific examples, which are included for purposes of illustration only and are not intended to be limiting unless otherwise specified.

PREPARATION OF CATALYSTS

Catalyst - 1

A 10 ml amount of silica (16-30 mesh, manufactured by Nikki Kagaku K.K.,N-608) was dipped into a solution of 0.558 g of antimonyl potassium tartrate ($C_4H_4KSbO_7 \cdot \frac{1}{2}H_2O$) in 10 ml of water and the mixture was condensed and dried by a rotary evaporator under reduced pressure. The mixture was then calcined to 400°C in an electric furnace while flowing oxygen at a rate of 1 liter per minute to obtain a pale yellowish-white solid product. The solid product was dipped into a solution of 0.238 g of palladium acetate dissolved in glacial acetic acid and the mixture was condensed and dried by a rotary evaporator under reduced pressure. The product was dried at 150°C in an electric furnace while flowing nitrogen and then was reduced at 150°C for 15 minutes under a flowing hydrogen atmosphere to prepare a catalyst which contained the following metal components (based on weight of carrier):

| | |
|---|---|
| Palladium | 2 wt. % |
| Antimony | 4 wt. % (as metal) |
| Potassium | 3 wt. % (as potassium acetate) |

Catalyst - 2

The process of Catalyst 1 was repeated except that 5 ml of a 10% aqueous solution of palladium nitrate containing 0.10 g of palladium was used as the palladium source. The catalyst containing the following components was obtained (based on weight of carrier):

| | |
|---|---|
| Palladium | 2 wt. % |
| Antimony | 4 wt. % (as metal) |
| Potassium | 3 wt. % (as potassium acetate) |

Catalyst - 3

A 10 ml amount of 16–20 mesh silica (the same as that of Catalyst - 1) was dipped into 30 ml of a hot solution of 0.417 g of potassium pyroantimonate ($K_2H_2Sb_2O_7 \cdot 4H_2O$). The mixture was condensed and dried by a rotary evaporator under reduced pressure to obtain a solid product having the same white color as the silica and which was substantially not powdered or peeled. The solid product was calcined at 400°C under flowing air. The product was dipped into a solution prepared by diluting 1.0 ml of 10% aqueous solution of palladium nitrate and the mixture was concentrated and dried by a rotary evaporator. The product was dried at 150°C under flowing nitrogen and then reduced at 150°C under flowing hydrogen to prepare the catalyst which contained the following metal components (based on weight of the carrier):

| | |
|---|---|
| Palladium | 2 wt. % |
| Antimony | 4 wt. % (as metal) |
| Potassium | 3 wt. % (as potassium acetate) |

Catalyst - 4

A 10 ml amount of 16 - 30 mesh silica (the same as that of Catalyst - 1) was dipped into 10 ml of an aqueous solution of 0.558 g of antimonyl potassium tartrate and 0.217 g of palladium nitrate. The mixture was concentrated and dried by a rotary evaporator under reduced pressure. The product was dipped into a solution of 15% of hydrazine hydrate and ammonia water to reduce it at 80°C for 6 hours. The resulting gray solid product was washed with water and was dipped into an aqueous solution of 0.102 g of zinc acetate. The mixture was condensed and dried by a rotary evaporator under reduced pressure to prepare the catalyst which contained the following components (based on weight of carrier):

| | |
|---|---|
| Palladium | 2 wt. % |
| Antimony | 4 wt. % (as metal) |
| Zinc acetate | 2 wt. % |

Catalyst - 5

A 10 ml amount of crushed active carbon (20–50 mesh) was dipped into 8 ml of an aqueous solution of 0.495 g of antimonyl potassium tartrate and the mixture was concentrated and dried by a rotary evaporator under reduced pressure. It was then calcined at 400°C for 1 hour in an electric furnace under flowing nitrogen containing 2% oxygen at a rate of 2 liters per hour. The product was dipped into 8 ml of an aqueous solution of palladium nitrate containing 0.10 g of palladium. The mixture was concentrated, dried and reduced at 150°C for 15 minutes under flowing hydrogen at the rate of 2 liters per hour.

Catalyst - 6

A 15 ml amount of 16–30 mesh silica (the same as that of Catalyst - 1) was dipped into a solution prepared by dissolving 0.736 g of antimony oxide and 2.274 g of tartaric acid in hot water. The mixture was concentrated and dried by a rotary evaporator under flowing oxygen and it was then calcined at 400°C for 1 hour. 10 ml of the calcined product was dipped into 5 ml of an aqueous solution of palladium nitrate containing 0.10 g of palladium and the mixture was concentrated and dried by a rotary evaporator. The product was dried at 150°C under flowing nitrogen and then reduced for 1 hour under flowing hydrogen. 0.103 g of zinc acetate was further supported on the product to prepare the catalyst which contained the following components (based on weight of carrier):

| Palladium | 2 wt. % |
| Antimony | 8 wt. % (as metal) |
| Zinc acetate | 2 wt. % |

Catalyst - 11

A 10 ml amount of silica (the same as that of Catalyst - 1) was dipped into a solution of 0.380 g of antimony trichloride and hydrochloric acid, and the mixture was dried by a rotary evaporator. Diluted ammonia water was gradually added to hydrolyze the compound. The supernatant solution was removed by decantation. The solid product was washed with water several times to remove hydrochloric acid. By this treatment, antimony hydroxide was separated from the carrier forming a white muddy solution. The carrier supporting the antimony compound was calcined under flowing oxygen at 400°C. whereby a small amount of powder was separated. The calcined product was dipped into an aqueous solution of palladium acetate and zinc acetate and the mixture was condensed and dried thereby supporting the latter constituents on the carrier. The product was then reduced under flowing hydrogen in accordance with the process of Catalyst - 1 to prepare the catalyst.

Catalyst - 12

A 10 ml amount of silica (the same as that of Catalyst - 1) was dipped in a conc. hydrochloric acid solution containing 0.380 g of antimony chloride and 84.6 mg of palladium chloride and the mixture was concentrated and dried. The product was dipped into a solution of hydrazine hydrate and ammonia water to reduce it at 80°C for 6 hours. The supernatant solution was removed by decantation. The solid product was washed with water and dried. The operation for supporting the palladium component and the antimony component was repeated. By the treatment, an antimony component containing palladium (pale gray) was separated. Zinc acetate was supported on the product by using an aqueous solution. A catalyst which contains the following components was prepared (based on weight of carrier):

| Palladium | 2 wt. % |
| Antimony | 8 wt. % (as metal) |
| Zinc acetate | 2 wt. % |

Catalyst - 13

A 50 ml amount of silica (the same as that of Catalyst - 1) was dipped into a solution prepared by dissolving 458 mmole of palladium chloride and 1600 mmole of antimony trichloride in 50 ml of aqua regia and the mixture was gradually condensed and dried by a rotary evaporator. The solid product was dipped into a 15% solution of hydrazine to reduce it at 40°C for 8 hours. The supernatant solution was removed by decantation. The solid product was washed with water, and then a solution of 7.47 mmole of zinc acetate dissolved in 75 ml of hot water was added to the product and the mixture was gradually condensed and dried by a rotary evaporator to prepare the catalyst.

Catalyst - 21

A 10 ml amount of silica (the same as that of Catalyst - 1) was dipped into a solution of 0.558 g of antimonyl potassium tartrate dissolved in 10 ml of water and the mixture was condensed and dried by a rotary evaporator under reduced pressure. The product was calcined at 800°C for 1 hour in an electric furnace under flowing oxygen at a rate of 1 liter per minute. The calcined product was dipped into 5 ml of an aqueous solution of palladium nitrate containing 0.10 g of palladium and the mixture was concentrated and dried by a rotary evaporator. The product was further dried at 150°C under flowing nitrogen and then reduced at about 150°C for 1 hour under flowing hydrogen at a rate of 0.5 liter per minute to prepare a catalyst which contained the following components (based on weight of carrier):

| Palladium | 2 wt. % |
| Antimony | 4 wt. % (as metal) |
| Potassium | 3 wt. % (as potassium acetate) |

Catalyst - 22

The process of Catalyst - 21 was repeated except that the calcination temperature was 600°C.

Catalyst - 23

A 10 ml amount of silica (the same as that of Catalyst - 1) was dipped into a solution prepared by dissolving 0.736 g of antimony trichloride and 2.274 g of tartaric acid in 15 ml of hot water and adding 5 ml of an aqueous solution of palladium nitrate containing 0.10 g of palladium. The mixture was condensed and dried by a rotary evaporator. The product was calcined at 600°C flowing passing oxygen for 1 hour and was reduced at 150°C by hydrogen. 0.103 g of zinc acetate was supported on the product to prepare the catalyst which contained the following components:

| Palladium | 2 wt. % |
| Antimony | 8 wt. % (as metal) |
| Zinc acetate | 2 wt. % |

Catalyst - 24

The process of Catalyst - 23 was repeated except that the calcination temperature was 600°C.

EXAMPLE 1

10 ml of each of the Catalysts 1, 2, 3, 11, 12 and 24 was placed in a reaction tube made of glass having an inner diameter of 20 mm. A gaseous mixture of isobutylene, oxygen, acetic acid and nitrogen present in the molar ratio of 18 : 2.7 : 2.7 : 13.5 : 65.8 was passed through the reaction tube at the reaction temperature of 130°–210°C in the space velocity of 1000 $hr^{-1}$, to effect the acetoxylation of isobutylene. The results are shown in Table 1.

TABLE 1

| Catalyst | Measurement | Unit | Val1 | Val2 | Val3 | Val4 | Val5 |
|---|---|---|---|---|---|---|---|
| Catalyst - 1 | Reaction temp. | °C | 139 | 168 | | | |
| | MAA[1] yield | mol/g-atom-Pd.hr | 1.56 | 2.41 | | | |
| | MPA[2] yield | " | 0.22 | 0.79 | | | |
| Catalyst - 2 | Reaction temp. | °C | 132 | 186 | | | |
| | MAA yield | mol/g-atom-Pd.hr | 1.52 | 2.99 | | | |
| | MPA yield | " | 0.60 | 0.88 | | | |
| Catalyst - 3 | Reaction temp. | °C | 140 | 162 | 190 | | |
| | MAA yield | mol/g-atom-Pd.hr | 1.94 | 3.03 | 3.59 | | |
| | MPA yield | " | 0.52 | 0.77 | 1.01 | | |
| Catalyst - 11 | Reaction temp. | °C | 152 | 176 | 200 | | |
| | MAA yield | mol/g-atom-Pd.hr | 0.86 | 1.44 | 1.85 | | |
| Catalyst - 12 | Reaction temp. | °C | 160 | 173 | 185 | 196 | 208 |
| | MAA yield | mol/g-atom-Pd.hr | 0.68 | 1.55 | 2.67 | 2.81 | 2.95 |
| Catalyst - 24 | Reaction temp. | °C | 168 | | | | |
| | MAA yield | mol/g-atom-Pd.hr | 2.75 | | | | |
| | MPA yield | " | 0.86 | | | | |

[1]MAA: methacryl acetate
[2]MPA: 2-methylene-1,3-propandiolacetate

EXAMPLE 2

A 10 ml amount of Catalyst - 5 was placed in the reaction tube of Example 1. A gaseous mixture of butene-1, oxygen, acetic acid and nitrogen at a molar ratio of 30 : 5 :24 :41 was passed through the reaction tube at the reaction temperature of 138°C in the space velocity of 587 $hr^{-1}$, to effect the acetoxylation of butene-1. The resulting product was hydrogenated at 50°C under atmospheric pressure for 2 hours in the presence of a 2% palladium carbon catalyst. The results are shown in Table 2.

TABLE 2

| | n-butyl acetate yield mmol/1-cat.hr | sec-butyl acetate yield mmol/1-cat.hr |
|---|---|---|
| Catalyst - 5 | 32.6 | 15.1 |

EXAMPLE 3

10 ml of each of the Catalysts 2, 6, 11, 13, 21 and 23 was placed in a reaction tube similar to that of Example 1. A gaseous mixture of benzene, oxygen and acetic acid at the molar ratio of 18 :4 :42 was passed through the reactor at the reaction temperature of 220°C in the space velocity of 1434 $hr^{-1}$ to effect the acetoxylation of benzene. The results are shown in Table 3.

TABLE 3

| | phenyl acetate yield mol/g-atom-Pd.hr |
|---|---|
| Catalyst - 2 | 5.38 |
| Catalyst - 6 | 3.98 |
| Catalyst - 11 | 3.45 |
| Catalyst - 13 | 3.47 |
| Catalyst - 21 | 6.61 |
| Catalyst - 23 | 5.54 |

EXAMPLE 4

10 ml of each of the Catalysts 2, 4, 6, 13, 21 and 22 was placed in a reaction tube similar to that of Example 1. A gaseous mixture of toluene, oxygen and acetic acid at the molar ratio of 15 :4 :42 was passed through the reaction tube at the reaction temperature of 220°C in the space velocity of 1366 $hr^{-1}$ to effect the acetoxylation of toluene. The results are shown in Table 4.

TABLE 4

| | Benzyl acetate yield mol/g-atom-Pd.hr |
|---|---|
| Catalyst-2 | 7.87 |
| Catalyst-4 | 6.33 |
| Catalyst-6 | 10.21 |
| Catalyst-13 | 6.40 |
| Catalyst-21 | 21.42 |
| Catalyst-22 | 30.36 |

EXAMPLE 5

10 ml of each of the Catalysts 1, 2, 13 and 22 was placed in a reaction tube similar to that of Example 1. A gaseous mixture of p-xylene, oxygen and acetic acid at a molar ratio of 13 :4 :42 was passed through the reaction tube at the reaction temperature of 220°C in the space velocity of 1322 $hr^{-1}$ to effect the acetoxylation of p-xylene. The results are shown in Table 5.

TABLE 5

| | xylylene diacetate yield mol/g-atom-Pd.hr | p-methyl benzyl acetate yield mol/g-atom-Pd.hr |
|---|---|---|
| Catalyst - 1 | 1.703 | 1.758 |
| Catalyst - 2 | 1.76 | 1.70 |
| Catalyst - 13 | 0.77 | 1.74 |
| Catalyst - 22 | 2.01 | 1.60 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for preparing a carboxylic ester by reacting benzene with an aliphatic saturated carboxylic acid having 2 to 4 carbon atoms and molecular oxygen in the vapor phase in the presence of a supported solid catalyst of palladium metal, antimony oxide and a carboxylic acid salt of an alkali metal, an alkaline earth metal, zinc, cadmium, lead or tin, the improvement comprising: adding said antimony oxide to the support of said catalyst by dipping a carrier into an aqueous solution of a water soluble antimony compound selected from the group consisting of antimonic acid, antimonates and antimony complexes of organic acids.

2. The process of claim 1, wherein the carrier is dipped into an aqueous solution of the water soluble antimony compound and then is calcined at 500° – 900°C in an oxygen-containing gas followed by dipping the product into an aqueous solution of a palladium compound.

3. The process of claim 2, wherein the calcination is performed at 600° – 800°C.

4. The process of claim 1, wherein the carrier is dipped in an aqueous solution of the water soluble antimony compound and the palladium compound and then the product is calcined at 500° – 900°C in an oxygen-containing gas whereby the antimony oxide and the palladium component are simultaneously supported.

5. The process of claim 4, wherein the calcination is performed at 600° – 800°C.

6. The process of claim 1, wherein the content of palladium supported on the carrier is 0.1 – 20% by weight.

7. The process of claim 1, wherein the catalyst contains 0.05 to 8 gram-atoms of antimony oxide as Sb and 0.1 to 8 moles of the carboxylic acid salt to 1 gram-atom of palladium.

8. The process of claim 1, wherein the catalyst contains 0.5 to 8 gram-atoms of antimony oxide as Sb and 0.5 to 4 moles of the carboxylic acid salt to 1 gram-atom of palladium.

9. The process of claim 1, wherein the molar ratio of the hydrocarbon to the carboxylic acid in the reaction is 1 :1 - 10.

10. The process of claim 1, wherein the reaction is conducted at 140° – 250°C.

11. In a process for preparing phenyl acetate by reacting benzene with acetic acid and oxygen in the vapor phase in the presence of a supported catalyst of palladium, antimony oxide and zinc acetate, the improvement comprising: adding said antimony oxide to the support of said catalyst by dipping a silica carrier into an aqueous solution of water soluble antimony compound selected from the group consisting of antimonic acid, antimonates and antimony complexes of organic acids, and then calcining the product at 500° to 900°C in an oxygen-containing gas.

12. The process according to claim 11, wherein the carrier supporting the antimony compound is calcined, dipped into an aqueous solution of the palladium compound to support the palladium compound and then the palladium compound is reduced at a temperature less than 200°C by hydrogen in the preparation of the catalyst.

13. The process of claim 11, wherein the calcination is conducted at 600° – 800°C.

14. The process of claim 11, wherein the silica carrier is dipped into an aqueous solution containing a palladium compound and said water soluble antimony compound.

15. The process of claim 11, wherein the catalyst contains 0.5–8 gram-atoms of the antimony component as Sb and 0.5–4 moles of zinc acetate to 1 gram-atom of palladium metal.

16. In a process for preparing a carboxylic ester by reacting benzene, acetic acid and molecular oxygen in the vapor phase in the presence of a supported catalyst of palladium, antimony oxide and potassium acetate, the improvement comprising: adding said antimony oxide to the support of said catalyst by dipping silica carrier in an aqueous solution of a water soluble antimony compound selected from the group consisting of antimonic acid, antimonates, and antimony complexes of organic acids and then calcining the product at 600°–800°C in an oxygen-containing gas.

17. The process according to claim 16, wherein the carrier supporting the antimony compound is calcined, dipped into an aqueous solution of the palladium compound to support the palladium compound and then the palladium compound is reduced at a temperature less than 200°C by hydrogen.

18. The process of claim 16, wherein the calcination is conducted at 600°–800°C.

19. The process of claim 16, wherein the silica carrier is dipped in an aqueous solution containing a palladium compound and said water-soluble antimony compound.

20. The process of claim 16, wherein the catalyst contains 0.5–8 gram-atoms of antimony oxide as Sb and 0.5–4 moles of potassium acetate to 1 gram-atom of palladium metal.

21. The process of claim 1, wherein the molecular oxygen is present in 1–50 mole percent of the total gaseous components.

* * * * *